US00PP24566P3

(12) United States Plant Patent
Austin

(10) Patent No.: US PP24,566 P3
(45) Date of Patent: Jun. 24, 2014

(54) ***ROSA HYBRIDA* SHRUB NAMED 'AUSBLANKET'**

(50) Latin Name: *Rosa hybrida*
Varietal Denomination: AUSblanket

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 133 days.

(21) Appl. No.: 13/506,556

(22) Filed: Apr. 27, 2012

(65) Prior Publication Data

US 2013/0061358 P1 Mar. 7, 2013

(51) Int. Cl.
*A01H 5/00* (2006.01)

(52) U.S. Cl.
USPC ..... Plt./104

(58) Field of Classification Search
USPC ..... Plt./104
See application file for complete search history.

(56) References Cited

U.S. PATENT DOCUMENTS

PP17,159 P2 * 10/2006 Austin ..... Plt./102
PP21,198 P2 * 8/2010 Kordes ..... Plt./102

OTHER PUBLICATIONS

UPOV PLUTO QZ Citation for 'AUSblanket' Dec. 15, 2011.*

* cited by examiner

*Primary Examiner* — Wendy C Haas
(74) *Attorney, Agent, or Firm* — KPPB LLP

(57) ABSTRACT

A variety of rose plant of the shrub class, named 'AUSblanket'. The 'AUSblanket' rose is a plant having a strongly fragrant myrrh scent, rounded buds that are rich butter yellow with red flashes developing into apricot blooms, maintaining the rounded chalice shape of the early bud, and being a particularly healthy shrub with few thorns.

1 Drawing Sheet

Classification: The present invention relates to a new *Rosa hybrida* shrub.

Variety denomination: The new plant has the varietal denomination 'AUSblanket'.

CROSS-REFERENCE TO RELATED APPLICATIONS

The current application claims priority to a European Community Plant Variety Application No. 2011/2133, filed Sep. 7, 2011, the disclosure of which is incorporated herein by reference.

ORIGIN OF INVENTION

This invention relates to a new and distinct variety of shrub rose plant named 'AUSblanket', which was originated from the cross-pollination of the two 'unnamed' and unpatented seedlings of *Rosa hybrida*.

BACKGROUND OF THE INVENTION

The primary objective of this breeding was to produce a variety of rose with an intense myrrh fragrance, and having rounded buds that are rich butter yellow with flashes of red, which develop into chalice shape blooms that are apricot in color overall.

SUMMARY OF THE INVENTION

Among the features which distinguish the new variety from others presently available and commercial rose cultivars known to the inventor is the following combination of characteristics: a strongly fragrant myrrh scent, rounded buds that are rich butter yellow with red flashes developing into apricot blooms, maintaining the rounded chalice shape of the early bud, and being a particularly healthy shrub with few thorns.

Asexual reproduction of the new variety by budding as performed outdoors at Bowling Green Lane in Albrighton, Britain shows that the foregoing and other distinguishing characteristics come true to form and are established and transmitted through succeeding asexual propagations. 'AUSblanket' may be asexually propagated by budding. The budding successfully occurred on the plant/rootstock *Rosa* cv. 'Dr. Huey' (not patented) in the United States, and *Rosa dumetorum* cv. 'Laxa' (not patented) for the observed plants in the UK.

COMPARISON WITH PARENTS

The seed and pollen parents of 'AUSblanket' are two unnamed seedlings. The new rose may be distinguished from its seed parent, by the following combination of characteristics: the new variety is rich butter yellow with flashes of red, which develop into apricot once fully opened, while the parent is pink, and the new variety has a rounded chalice shape bloom while the parent has a cupped bloom. The qualities of the pollen parent are unknown.

COMPARISON WITH THE CLOSEST COMMERCIALLY AVAILABLE CULTIVAR

The closest commercially available cultivars to the new variety are the 'AUSjo' (unpatented), which is available commercially under the tradename 'Jude the Obscure', and 'AUStwist' (unpatented), which is available commercially under the tradename 'The Shepherdess'. The new rose may be distinguished from the 'AUSjo' variety by the following combination of characteristics: the 'AUSblanket', which is available commercially under the tradename 'Wollerton Old Hall', has a bloom with hints of yellow, whereas in 'AUSjo' has a bright yellow color and 'AUStwist' has a soft apricot color. 'AUSblanket' also has a strong myrrh fragrance compared with 'AUSjo', which has a fruity fragrance, and 'AUStwist' is fruity with hints of lemon.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSblanket' specimens were made at a nursery in Albrighton, Wolverhampton, United Kingdom. The following description is of 1 year-old rose plants of the new variety grown outdoors in Albrighton, Britain in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but at any given time during the first flush in summer there are 8-16 blooms per plant. There are too many blooms over a full growing season to count.

Bud:

*Size*.—About 2 cm long and 1.8 cm in diameter when the petals start to unfurl.

*Form*.—The bud form is pointed short and globular.

*Color*.—When sepals first divide, the bud color is yellow-orange RHS 20B with flashes of red RHS 38A. When half blown, the upper sides of the petals are yellow-orange RHS 18A and the lower sides of the petals are yellow-orange RHS 18A (with the outer petals flashed with orange-red RHS 34B).

*Calyx*.—Shape: star-shaped when fully opened with the sepals folding back. Length: 4.4 cm. Diameter: 5 cm.

*Sepals*.—Arrangement: Regular. Color: Upper Surface: green RHS 143D. Lower Surface: green RHS 143C with some red-purple RHS 64B. Length: 32 mm. Width: 13 mm. Shape: Deltoid with extensions. Surface texture: Upper Surface: Downy. Lower Surface: Smooth. Number: There are 3 normally appendaged sepals, and 2 unappendaged sepals with hairy edges.

*Receptacles*.—Color: green RHS 143C. Shape: pitcher. Size: medium, about 1.3 cm×1 cm. Surface: Smooth.

*Peduncle*.—Length: short, averaging about 5 cm. Surface: Glandular. Color: light green RHS 143C. Strength: Normal.

*Bud leaves*.—Color: light green RHS 143C.

Blooms:

*Size*.—Medium, average open diameter is about 9.5 cm.

*Borne*.—Mostly singly in clusters of 1-4 blooms having flat inflorescence.

*Stems*.—Strength: Normal, average length is about 5 cm. Diameter: 1.5 mm.

*Form*.—When first open, bloom is globular. Permanence of bloom: retains its form to the end.

Petalage: Number of petals under normal conditions: 43.

*Color*.—The upper sides of the petals are yellow RHS 11C in the middle zone with orange RHS 27C at the tip. The reverse sides of the petals are yellow RHS 11C in the middle zone with orange RHS 27C at the tip.

*Variegations*.—Shading at the tip of the petals.

*Discoloration*.—The general tonality at the end of the first day is yellow RHS 11C with orange RHS 27C, and at the end of the third day is yellow RHS 11C with orange 27C.

*Fragrance*.—Strong. Character of fragrance: myrrh.

Petals:

*Texture*.—Smooth.

*Size*.—Width: 5.5 cm. Length: 6 cm.

*Surface*.—Smooth.

*Shape*.—Notched and obovate.

*Margin*.—Notched.

*Apex shape*.—Notched.

*Base shape*.—Obtuse.

*Form*.—Incurved.

*Arrangement*.—Imbricated.

*Petaloids*.—Number: 8. Color: RHS 11C+, RHS27C, and white RHS 155C. Length: 10-50 mm. Width: 4 mm. Shape: Obovate. Margin: Irregular.

*Persistence*.—Petals hang on and dry.

*Lastingness*.—On the plant: About 7 days. As a cut flower: Not tested.

Reproductive parts:

*Stamens*.—Number: 100. Length: 10 mm.

*Anthers*.—Length: 2 mm. Color: yellow-orange RHS 22A. Arrangement: regular around styles mostly, but a few are tucked in the calyx.

*Filaments*.—Color: yellow-orange RHS 22A. Length: 8 mm.

*Pollen*.—Color: yellow-orange RHS 22A.

*Pistils*.—Number: 30. Length: 3.5 mm.

*Styles*.—Color: yellow with some pink (RHS 22B & RHS 47C). Length: 3 mm.

*Stigmas*.—Color: yellow-orange RHS 22B. Length: 0.5 mm.

*Hips*.—None Observed.

PLANT CHARACTERISTICS

Plant form: Shrub.

Plant growth: Vigorous, upright and branching.

Age to maturity: Two years.

Mature plant: Height: 150 cm. Width: 100 cm.

Rootstock: *Rosa* cv. 'Dr. Huey' in the United States, *Rosa dumetorum* cv. 'Laxa' for the observed plants in the UK.

Foliage:

*Number*.—Leaflets on normal mid-stem leaves is: 15.

*Size*.—Medium, about 14 cm long×10.5 cm wide.

*Quantity*.—Normal. Number of leaves per flowering stem is: 14.

*Color*.—New foliage: Upper side: yellow/green RHS 146B. Lower side: yellow/green RHS 146C. Old foliage: Upper side: yellow/green RHS 147A. Lower side: yellow/green RHS 146B.

Leaflets:

*Size*.—About 14 cm long×10.5 cm wide.

*Shape*.—Broadly oval.

*Base shape*.—Rounded.

*Apex shape*.—Acuminate.

*Texture*.—Leathery.

*Edge*.—Serrated.

*Serrations*.—Single and large.

*Petiole*.—Color: yellow-green RHS 146B. Length: 6 cm. Width: 2 mm. Surface Texture: Rough.

*Petiole rachis*.—Color: green RHS 146B. Underside: with prickles.

*Stipules*.—Length: 2.5 cm, glandular. Color: 146C.

*Auricle*.—Shape: Lanceolate. Length: 0.5 cm. Width: 2 mm. Color: RHS 146B.

*Vein color*.—RHS 146B & RHS 179A.

*Venation pattern*.—Reticulate (net-veined).

Wood:

*New wood*.—Color: violet-red RHS 179A. Bark: Smooth.

*Old wood*.—Color: dark-green RHS 146B. Bark: Smooth.

Branching habit:

*Number*.—10.

*Lateral branch dimensions*.—Length: 60 cm. Diameter: 7 mm.

Stems:

*Mature stem*.—Length: 80 cm. Diameter: 9 mm.

*Internode distance*.—7 cm. The above measurements are all variable, depending on growing conditions in a season.

*Stem pubescence present*.—No.

*Stem color*.—RHS 146B.

Prickles:

*Quantity*.—On main canes from base: Few. Number per stem length: 6 per 30 cm. On laterals from main canes: Few. Number per stem length: 6 per 30 cm.

*Form*.—Deep concave.

*Length*.—7 mm.

*Color when young*.—Red RHS 179A.

*Color when mature*.—Brown RHS 177C.

Small prickles:

*Quantity*.—Main stalk: None Number per stem length: N/A. Laterals: Few Number per stem length: N/A.

*Color*.—When young: red RHS 179A. When mature: Brown RHS 177C.

Disease resistance:

*Mildew*.—Resistant to Powdery Mildew and Downy Mildew.

*Blackspot*.—Resistant.

*Rust*.—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

* * * * *

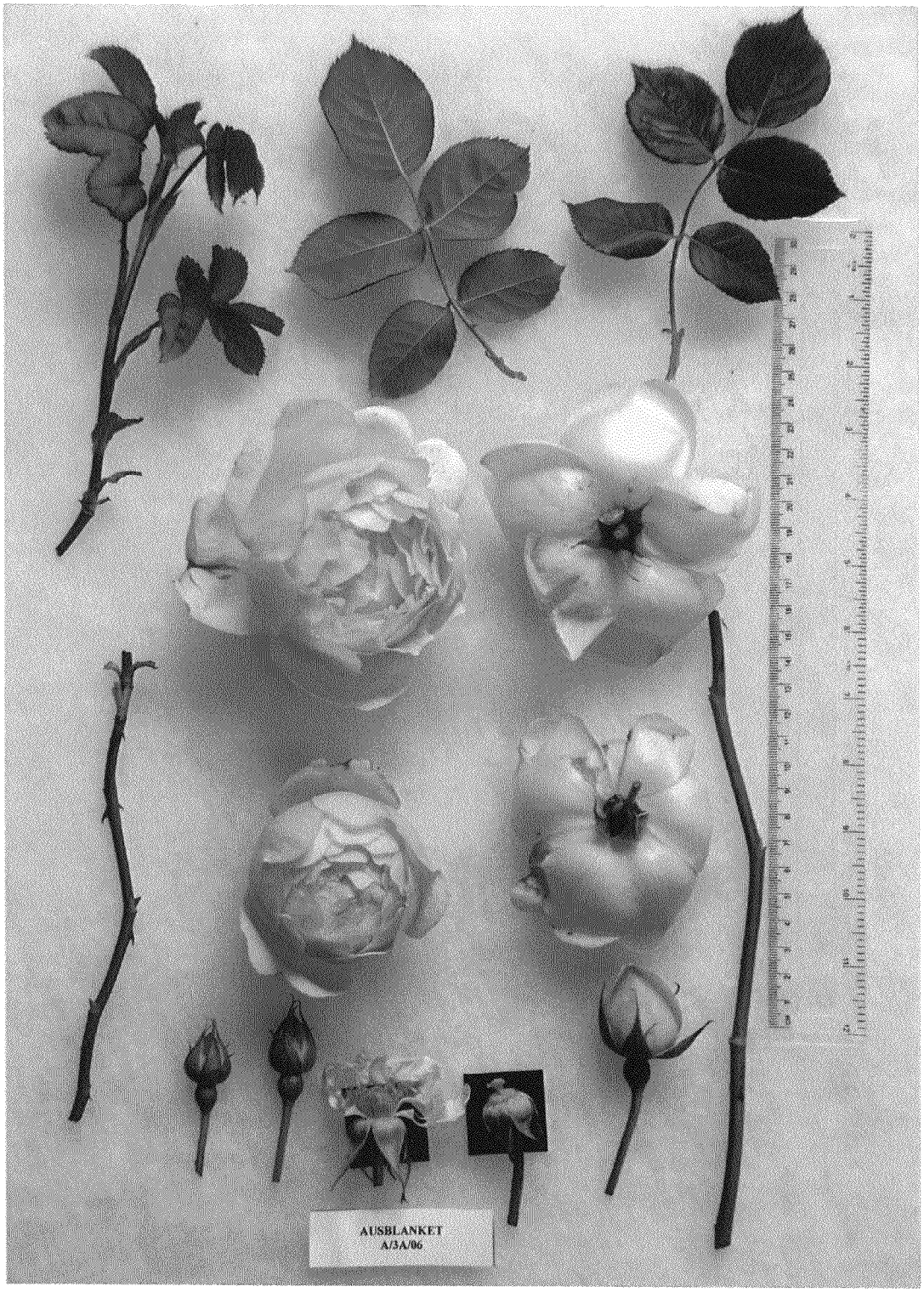
AUSBLANKET
A/3A/06